(12) United States Patent
Brocia

(10) Patent No.: US 6,174,693 B1
(45) Date of Patent: Jan. 16, 2001

(54) IMMUNOLOGICAL ASSAY FOR PROTEIN ACTIVITY

(76) Inventor: Robert W Brocia, 15 Moore Rd., Bronxville, NY (US) 10708

( * ) Notice: Under 35 U.S.C. 154(b), the term of this patent shall be extended for 0 days.

(21) Appl. No.: 09/005,875

(22) Filed: Jan. 12, 1998

(51) Int. Cl.[7] .................................................. G01N 33/533
(52) U.S. Cl. .............................. 435/7.4; 435/4; 435/7.72; 435/11; 436/501; 436/518
(58) Field of Search ...................................... 435/7.4, 7.72, 435/4, 11; 436/501, 518

(56) References Cited

U.S. PATENT DOCUMENTS

| | | | |
|---|---|---|---|
| 5,196,306 | * | 3/1993 | Bobrow et al. ........................ 435/7.9 |
| 5,296,347 | * | 3/1994 | LaMotte, III ............................. 435/5 |
| 5,585,235 | * | 12/1996 | Brocia ....................................... 435/4 |

* cited by examiner

*Primary Examiner*—Donna C. Wortman
(74) *Attorney, Agent, or Firm*—Carmella A. O'Gorman

(57) ABSTRACT

An immunological method to determine protein activity wherein a variety of proteins may be assayed with a single antibody on standard equipment is provided.

1 Claim, 1 Drawing Sheet

IMMUNOLOGICAL ASSAY FOR PROTEIN ACTIVITY

BACKGROUND OF THE INVENTION

This invention relates generally to the field of immunoassays. More particularly, the invention is an immunological method and apparatus that measures the activity of an enzyme.

There are no known immunological methods to determine protein activity.

BRIEF SUMMARY OF THE INVENTION

Accordingly, a brief summary of the instant invention is that it measures an enzyme by utilization of antibodies to the enzyme substrate.

According to one aspect of the present invention there is provided a means to permit the activity measurement of a variety of enzymes using one antibody.

According to a further aspect of the present invention there is provided a means to screen for compounds that change the activity of a protein. Still further objects and advantages will become apparent from a consideration of the ensuing description and accompanying drawings.

DETAILED DESCRIPTION

Figure 1:
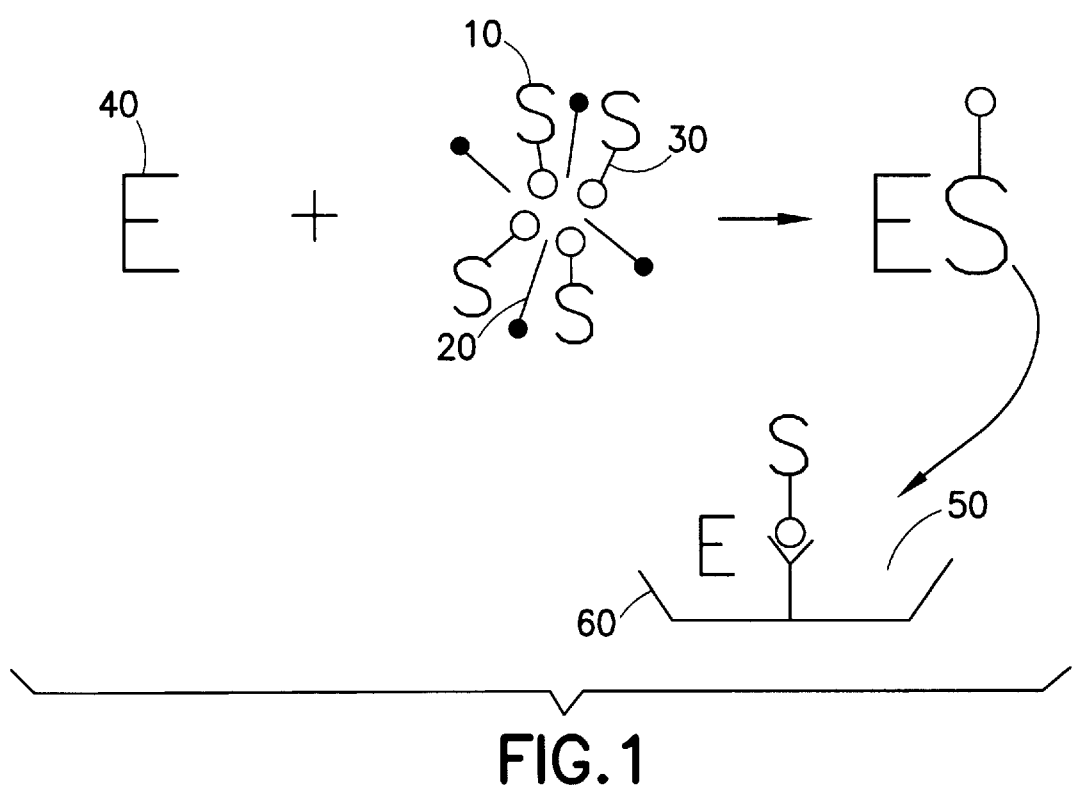
FIG. 1 is a diagram of the activity assay according to the present invention.

Immunoassays are typically used as a means of determining the amount of a specific protein in a sample that may be a mixture of many different proteins. Immunoassays do not give any information concerning the activity of the protein.

The present invention is an immunological method that measures the activity of a protein by utilizing a standard assay platform compatible with conventional instrumentation.

The enzyme may be included in a mixture of proteins. For example, it may be present in plasma or serum or similar bodily fluid including cellular extracts.

The invention includes incubation of a sample comprised of the enzyme of interest with a first component of the invention; this maybe referred to as the first component interaction of the invention. The first component is comprised of a reactant or substrate of the enzyme. The first component is further comprised of a covalently bound antigenic factor. According to the invention, the first component interaction is not an immunological interaction. In fact, the first component is not necessarily a protein. The first component may be a protein when the invention is applied to activity determination of proteases or other enzymes that utilize proteins as substrates. The first component interaction is followed by a second component interaction which includes a second component of the invention. The second component interaction is an immunological interaction and the second component is an antibody. The second component is an antibody specific for the antigenic factor of the first component.

A preferred embodiment of the invention includes the measurement of a protein's activity where the protein is a lipid transfer protein. The lipid transfer protein is incubated with a substrate of the protein in a suitable substrate donor format such as an emulsion or liposome. In the case of activity measurement of plasma lipid transfer proteins such as cholesteryl ester transfer protein (CETP), the first component is cholesteryl ester that is fluorescently labeled, such as 22-(N-(7-nitrobenz-2-oxa-1,3-diazol-4-yl)amino)-23,24-bisnor-5-cholen-3-yl linoleate (NBD-CE). The antigenic factor is NBD in the case of the substrate NBD-CE comprising the first component of the invention. Other fluorescent labels such as fluorescein or rhodamine may be used as antigenic factors. The second component of the invention is an antibody to NBD. The lipid transfer protein transfers the substrate from the donor to the antibody. The antibody is specific for NBD.

The invention is used to measure the activity of proteins that transfer a substrate from one location (substrate donor) to another location (substrate acceptor). For example in FIG. 1, in the case of the neutral lipid transfer proteins including cholesteryl ester transfer protein and triglyceride (TG) transfer protein or phospholipid transfer protein the substrate donor 10 includes an emulsifier 20 and labeled substrate 30 in a particle that requires the protein 40 to remove the substrate from the particle in order for binding to antibody 50 to occur. The antibody then is an acceptor for the transfer process. The protein /donor/antibody incubation takes place in a buffered solution at a pH acceptable to the protein to effectively transfer substrate. The second component is bound to a microplate well 60 which allows washing the well plate with buffer to remove donor and sample leaving bound substrate. The plate is read in a fluorimeter to determine the amount of substrate bound to the antibody.

The transfer from donor to acceptor antibody may also be effected by an intermediate lipid acceptor of a synthetic origin. A suitable synthetic acceptor includes a phospholipid/triglyceride emulsion or a crude lipid emulsion. The CETP is known to be involved in a hetero exchange where CE is exchanged for TG at the acceptor. In the case of the neutral lipid transfer proteins, the emulsified labeled substrate is incubated with the lipid transfer protein LTP and a synthetic or non-synthetic TG "sink" that supports the hetero-exchange process and donates neutral lipid to the protein. The antibody is also present so that the immunoactively labeled substrate will bind to antibody. The antibody may partition into the intermediate acceptor.

Phospholipid transfer activity is determined in a similar manner to CETP except a liposome donor may be used in the first component interaction and an NBD labeled phospholipid is the first component of the invention. Similarly phospholipases may also be assayed when the NBD label is on an acyl chain of the phospholipid. Cleavage of the phospholipid by a phospholipase releases an NBD labeled fatty acid which will bind to the NBD antibody second component.

CONCLUSIONS, RAMIFICATIONS, AND SCOPE

Accordingly, it can be seen that the present invention allows activity measurement of a variety of proteins utilizing one antibody.

Although the description above contains many specificities, these should not be construed as limiting the scope of the invention but as merely providing illustrations of some of the presently preferred embodiments of this invention. Various other embodiments and ramifications are possible within it's scope. For example, use of the invention to identify inhibitors of enzymes.

Thus the scope of the invention should be determined by the appended claims and their legal equivalents, rather than by the examples given.

I claim:

1. A method to determine the activity of a protein in a light emitting assay comprising the steps of:

non-immunologically contacting said protein with a first component, wherein said first component comprises a labeled substrate of said protein;

immunologically interacting said first component with a second component, wherein said second component comprises an antibody specific for the label of said labeled substrate;

and measuring a change in light emission from said assay to determine the activity of said protein.

* * * * *